US005686294A

United States Patent [19]

Sogabe et al.

[11] Patent Number: 5,686,294
[45] Date of Patent: Nov. 11, 1997

[54] PROTEIN HAVING HEAT-RESISTANT MALATE DEHYDROGENASE ACTIVITY

[75] Inventors: Atsushi Sogabe; Seiji Takeshima; Kazumi Yamamoto; Shinichi Teshima; Shigenori Emi; Yoshihisa Kawamura, all of Tsuruga, Japan

[73] Assignee: Toyo Boseki Kabushiki Kaisha, Osaka, Japan

[21] Appl. No.: 270,013

[22] Filed: Jul. 1, 1994

[30] Foreign Application Priority Data

Jul. 2, 1993 [JP] Japan .................................. 5-164701

[51] Int. Cl.$^6$ .............................. C12N 15/53; C12N 9/04
[52] U.S. Cl. .............................. 435/252.3; 435/320.1; 435/252.31; 435/252.33; 435/190; 536/23.2
[58] Field of Search .......................... 435/190, 320.1, 435/252.33, 252.31; 536/23.2; 935/10, 14

[56] References Cited

PUBLICATIONS

Birkraft et al., "The Presence of a Histidine–Aspartic Acid pair in the Active Site of 2-Hydroxyacid Dehydrogenases", *J. Biol. Chem.*, 258: 472 (1983).

Sundaram et al., "Malate Dehydrogenase from Thermophilic and Mesophilic Bacteria Molecular Size, Subunit Structure, Amino Acid Composition, Immunochemical Homology, and Catalytic Activity", *Biochemistry*, 19, 2017–2022 (1980).

Murphey et al., "Purification and Propertieis of Bacillus Subtilis, Bacillus Stearothermophilus, and Escherichia Coli Malate Dehydrogenases", *The Journal of Biological Chemistry*, 242, No. 7, 1548–1559 (1967).

Rolstad et al., "Malate Dehydrogenase from the Thermophilic Green Bacterium Chloroflexus aurantiacus: Purification, Molecular Weight, Amino Acid Composition, and Partial Amino Acid Sequence", *Journal of Bacteriology*, 170 No. 7, 2947–2953 (1988).

Ohshima et al., "Purification and Characterization of Malate Dehydrogenase from the Phototrophic Bacterium, Rhodopseudomonas Capsulata", *Biochimica et Biophysica Acta*, 869, 171–177 (1986).

You et al., "Purification and Properties of Malate Dehydrogenase from Pseudomonas Testosterni", *Journal of Bacteriology*, 123, No. 2, 704–716 (1975).

Iijima et al., "Physiochemical and Catalytic Properties of Thermostable Malate Dehydrogenase From an Extreme Thermophile Thermus Flavus at 62", *Biochemica et Biophysica Acta*, 613, 1–9 (1980).

Lepock et al. *Biochimica et Biophysica Acta*, 1990, vol. 1055, pp. 19–26.

Wright et al. *Biochem J.*, 177:441–448, 1979.

Wilks et al., *Science*, vol. 242, pp. 1541–1544, 16 Dec. 1988.

Sambrook et al. *Molecular Sloning: A Laboratory Manual*, 1989, Cold Spring Harbor Press, pp. 11–3–11.19.

*Primary Examiner*—Keith D. Hendricks
*Attorney, Agent, or Firm*—Leydig, Voit & Mayer, Ltd.

[57] ABSTRACT

A novel protein having a heat-resistant malate dehydrogenase activity, a DNA fragment having a gene encoding said protein, a recombinant vector having said DNA fragment, a transformant transformed with said vector, a method for producing the protein having heat-resistant malate dehydrogenase activity by the use of said transformant, a reagent for GOT determination, comprising the above-mentioned novel protein having a heat-resistant malate dehydrogenase activity and a method for determining GOT activity, which comprises the use of said reagent. According to the present invention, a protein having a heat-resistant malate dehydrogenase activity and having higher purity and superior heat stability can be obtained. In addition, a reagent for GOT determination which is superior in long-term storage can be prepared by the use of the protein having a heat-resistant malate dehydrogenase activity.

15 Claims, 3 Drawing Sheets

PROTEIN HAVING HEAT-RESISTANT MALATE DEHYDROGENASE ACTIVITY

FIELD OF THE INVENTION

The present invention relates to a novel protein having a heat-resistant malate dehydrogenase activity, which is useful for the determination of glutamic-oxaloacetic transaminase (hereinafter referred to as GOT) activity in blood that is a clinical index for diagnoses of hepatitis and myocardinal infarction and for the measurement of carbon dioxide concentration in plasma that is an index of acid-base imbalance in the respiratory metabolism; a DNA fragment having a gene encoding said protein; a recombinant vector having said DNA fragment; a transformant transformed with said vector; and a method for producing a protein having a heat-resistant malate dehydrogenase activity by using said transformant.

The present invention also relates to a reagent for determining GOT activity, which comprises, as one component, the above-mentioned novel protein having a heat-resistant malate dehydrogenase activity and to a method for determining GOT activity, which comprises the use of said reagent.

BACKGROUND OF THE INVENTION

Malate dehydrogenase (EC 1.1.1.37) is an enzyme which is widely present in animal, plant and microbial sources and is conventionally used in clinical tests, for instance, to determine the GOT activity in blood or carbon dioxide concentration in plasma.

As said enzyme, a malate dehydrogenase derived from the mitochondria of swine heart is generally used. Since the malate dehydrogenase of swine heart is poor in thermalstability, the commercially available reagents for GOT activity measurement comprising said malate dehydrogenase are not satisfactory in that the reagent cannot be stored for a long time in a liquid state.

On the other hand, various malate dehydrogenases derived from bacteria have been found. It is known that mesophilic bacteria such as *Corynebacterium, Brevibacterium* and Arthrobacter (Japanese Patent Unexamined Publication No. 26396/1979), *Bacillus subtills* and *Escherichia coli* [J. Biol. Chem., vol. 242, No. 7, 1548–1559 (1967)], *Choloroflexus aurantica* [J. Baeteriol., vol. 170, No. 7, 2947–2953, July (1988)], *Rhodopsuedomonas capsulata* [Bioehimica et Biophysica Acta, 869, 171–177 (1986)], and *Pseudomonas testosterni* [J. Baeteriol., vol. 123, No. 2, 704–716, August (1975)] produce malate dehydrogenases which are not heat-resistant. None of them are sufficient in heat stability or have high productivity to realize their practical applications.

It is also known that thermophilie bacteria such as *Thermus thermophilus* (Japanese Patent Unexamined Publication No. 99188/1980), *Thermus Flavus* AT-62 [Biochimica et Biophysica Acta, 613, 1–9 (1980), *Bacillus stearothermophilus* strain UK 788 (Japanese Patent Unexamined Publication No. 148288/1981 corresponding to U.S. Pat. No. 4,331,762) and *Bacillus stearothermophilus* strain 2184 [J. Biol. Chem., vol. 242, No. 7, 1548–1559 (1967)] produce heat-resistant malate dehydrogenases. The malate dehydrogenase derived from the genus Thermus sp. is being sold as a heat stable enzyme. The optimum temperature of this enzyme, however, is as high as around 90° C. and it exhibits low catalytic activity at a temperature near the reaction temperature (generally room temperature) to be employed in clinical tests, thus rendering application of this enzyme to clinical tests unsuitable. The enzyme, moreover, has been found to be not so superior in stability in a reagent for determining GOT activity as is expected from the heat stability that the enzyme has.

The thermal property of the malate dehydrogenase derived from the genus *Bacillus stearothermophilus* strain UK 788 is not certain. As the strain produces other enzymes like heat-resistant acetate kinase together with a malate dehydrogenase, there is a possibility that the purified malate dehydrogenase may be contaminated.

*Bacillus stearothermophilus* strain 2184 also produces heat resistant malate dehydrogenase. But the maximal specific activity assayed at 22° C. for the enzyme of this strain is very low due to its poor activity at this temperature. Therefore, these enzymes derived from *Bacillus stearothermophilus* strains may not have sufficiently high productivity to allow preparation of the reagents for determining GOT activity or may not be superior in stability during long-term preservation.

Accordingly, a malate dehydrogenase superior in reactivity at room temperature and stability during long-term preservation, particularly stability in a reagent for GOT determination, is desired.

SUMMARY OF THE INVENTION

A first object of the present invention is to provide a protein having a heat-resistant malate dehydrogenase activity, which exhibits superior stability in a reagent for determining GOT activity.

A second object of the present invention is to provide a process and materials for supplying said protein in a pure form and in a large amount by genetic engineering.

A third object of the present invention is to provide a reagent for determining GOT activity, which comprises, as one component, the protein of the present invention having a heat-resistant malate dehydrogenase activity.

A fourth object of the present invention is to provide a method for determining GOT activity, which comprises the use of the protein of the present invention having a heat-resistant malate dehydrogenase activity.

With the aim of achieving the aforementioned objects, the present inventors have conducted various studies and found that *Bacillus stearothermophilus* ATCC 12016 has a gene encoding a protein having a heat-resistant malate dehydrogenase activity, and isolated the gene from the chromosomal DNA of the cells thereof, based on which the entire nucleotide sequence has been successfully identified. Further studies resulted in the finding that a transformant into which the gene derived from said *Bacillus stearothermophilus* ATCC 12016 by genetic engineering has been introduced produces, at high yields, a protein having a heat-resistant malate dehydrogenase activity and exhibiting higher heat resistance and higher specific activity than do the protein produced by the *Bacillus stearothermophilus* ATCC 12016. The studies also resulted in the establishment of a method for producing said protein in a highly purified form at high yields. In the following specification, said protein having a heat-resistant malate dehydrogenase activity of the present invention is also referred to simply as heat-resistant MAD.

DETAILED DESCRIPTION OF THE INVENTION

According to the present invention, there is provided a protein having a heat-resistant malate dehydrogenase activity, which exhibits a residual activity after preservation at 40° C. for 10 days in a solution state of at least 60%.

In addition, the present invention provides a DNA fragment comprising a gene encoding a protein having a heat-resistant malate dehydrogenase activity; a recombinant vector having said DNA fragment; a transformant transformed with said recombinant vector; and a method for producing the protein having a heat-resistant malate dehydrogenase activity, which comprises culturing said transformant in a medium to allow production of the protein having a heat-resistant MAD activity and collecting said protein.

The present invention further provides a reagent for determining GOT activity, comprising NADH, L-aspartic acid, α-ketoglutaric acid, (optionally lactate dehydrogenase) and heat-resistant malate dehydrogenase exhibiting a residual activity after preservation at 40° C. for 10 days in a solution state of at least 60%.

The present invention also provides a method for determining GOT activity, comprising measuring NADH consumed by the GOT measurement reagent comprising NADH, L-aspartic acid, α-ketoglutaric acid, (optionally lactate dehydrogenase) and heat-resistant MAD exhibiting a residual activity after preservation at 40° C. for 10 days in a solution state of at least 60%.

It is essential that the protein having a heat-resistant malate dehydrogenase activity should exhibit a residual activity after preservation at 40° C. for 10 days in a solution state of at least 60%, preferably 70%, more preferably 80% and most preferably 90%.

In the present invention, "a solution state" refers to a solution having the following formulation.

| | |
|---|---|
| Lactate dehydrogenase (optionally used) | 500–2000 U/l |
| Heat-resistant malate dehydrogenase | 500–5000 U/l |
| L-Aspartic acid | 150–250 mmol/l |
| α-Ketoglutaric acid | 10–40 mmol/l |
| NADH | 0.1–0.25 mmol/l |
| Buffer (pH 7.5) | 0.05–0.1 mmol/l |

The residual activity as referred to in the present invention is a ratio (%) of the activity of malate dehydrogenase after preservation of the above-mentioned solution at a given temperature for 10 days, to the MAD activity (100%) before the preservation.

The activity of malate dehydrogenase is measured as in the following.

The following reaction mixture is placed in a cuvette (d=1.0 cm) and pre-heated at 25° C. for about 5 minutes.

| | | |
|---|---|---|
| 0.1 M | K-oxaloacetate buffer (pH 7.5) | 2.8 ml |
| 15 mM | oxaloacetic acid solution (dissolved in K-phosphate buffer) | 0.1 ml |
| 6.0 mM | NADH aqueous solution | 0.1 ml |

A solution (0.05 ml) containing the aforementioned heat-resistant MAD is added to the reaction mixture as described above and the mixture is gently mixed. The change in absorbance at 340 nm is measured at 25° C. for 3–4 minutes with a spectrophotometer using water as a control and the change in absorbance per minute is determined from the initial linear portion thereof (ΔOD test). As a blank test, the change in absorbance per minute is determined by doing the same test as above except that 0.05 ml of K-phosphate buffer (pH 7.5) is added in place of the solution containing heat-resistant MAD (ΔOD blank). The MAD 1U (unit) is the amount of the enzyme necessary for oxidizing 1 μmol of NADH per minute under the above-mentioned conditions.

The heat-resistant MAD is not subject to any particular limitation insofar as it has the aforementioned properties and the origin thereof is not limited. Preferably, it is a heat-resistant MAD produced by *Bacillus stearothermophilus* ATCC 12016 strains and more preferably, a heat-resistant MAD produced by a transformant carrying a gene encoding heat-resistant MAD, which is derived from a bacterium belonging to the genus Bacillus, in view of superior heat stability and specific activity to the heat-resistant MAD produced by the ATCC 12016 strains.

The transformant carrying a gene encoding the heat-resistant MAD is not subject to any particular limitation insofar as it is capable of producing the heat-resistant MAD. Preferred are those derived from *Eschelichia coli* or *Bacillus subtilis* and more preferred are those derived from *E. coli* W3110, *E. coli* C600, *E. coli* JM109, *Bacillus subtilis* MI113 or *Bacillus subtilis* MT-2.

The gene encoding the heat-resistant MAD, which is carried by the transformant, may be isolated from a bacterium belonging to the genus Bacillus by a conventional method or may be chemically synthesized. The gene may be of wild type or non-wild type as long as it is capable of encoding the heat-resistant MAD, and is exemplified by a DNA sequence obtained by partial mutation of a wild type DNA sequence of a gene encoding heat-resistant MAD, which is derived from a bacterium belonging to the genus Bacillus.

Preferred gene is a nucleotide sequence having a gene encoding the amino acid sequence depicted in the SEQ ID NO:2, more preferably that having a nucleotide sequence depicted in the SEQ ID NO:1 to be given later.

The heat-resistant MAD of the present invention preferably has the following properties.

Action: reversibly eatalyzes the following reaction.

L-malic acid+NAD⁺—oxaloacetic acid+NADH+H⁺

Substrate specificity: specifically oxidizes L-malic acid or specifically reduces oxaloacetic acid.

Optimum temperature: 70° C.

Optimum pH: 8.0

Heat stability: not more than 70° C.

pH Stability: pH 3.0–9.0

Isoelectric point: 4.8

Molecular weight: 140,000 (gel filtration), 38,000 (SDS-PAGE)

Km value: $4.3 \times 10^{-6}$ M (oxaloacetic acid)

Specific activity: 203 U/mg protein

The method for obtaining the heat-resistant MAD of the present invention is not limited. For example, a *Bacillus stearothermophilus* ATCC 12016 strain or a transformant carrying a gene encoding heat-resistant MAD may be cultured by a conventional method and the heat-resistant MAD yielded is harvested from the culture, or the heat-resistant MAD may be chemically synthesized by a conventional method.

In the following, an exemplary method for obtaining the heat-resistant MAD of the present invention from a *Bacillus stearothermophilus* ATCC 12016 strain is given.

The medium for culturing said strain may be that containing carbon source, nitrogen source, inorganic ion and where necessary, nitrate, phosphate etc. As the carbon source, usable are sugars from monosaccharides such as glucose and fructose to macromolecular polysaccharides such as dextrin and soluble starch. As the nitrogen source, exemplified are polypepton, trypton, meat extract and yeast extract. Culture is performed until the yield of the malate dehydrogenase reaches maximum at a temperature affording the highest growth of the cells.

The malate dehydrogenase can be isolated from the culture cell and purified as in the following.

Cells are collected by centrifugation of the culture. The cells are disrupted to enable extraction of the malate dehydrogenase. For disrupting, a cell wall lytic enzyme such as lysozyme may be used or physical treatment such as ultrasonication, glass beads disruption or French press disruption may be applied.

The lysate thus obtained is subjected to denucleation by a treatment with polyethyleneimine and a malate dehydrogenase fraction is recovered by ammonium sulfate fractionation. The malate dehydrogenase fraction thus obtained is desalted by G-25 gel filtration and purified to a higher degree by DEAE Sepharose CL-6B column chromatography (Pharmacia LKB, Sweden)→Phenyl Sepharose CL-6B column chromatography (Pharmacia LKB, Sweden)→TSK gel G-3000 SW gel (Toyo Soda, Japan) filtrations and MonoP HR5/5 chromatofocusing (Pharmacia LKB, Sweden). The purified product migrates as a single band on SDS polyacrylamide gel electrophoresis (SDS-PAGE). While the combination of the column chromatographys is not limited to that mentioned above, several steps of column chromatographies may be necessary for achieving a single band on electrophoresis.

The DNA fragment of the present invention is subject to no particular limitation insofar as it has a nucleotide sequence encoding the heat-resistant MAD as described earlier. For example, a DNA fragment comprising a nucleotide sequence encoding the amino acid sequence as listed in SEQ ID NO:2 or a DNA fragment comprising a nucleotide sequence as listed in SEQ ID NO:1 may be used. In addition, a DNA fragment having a nucleotide sequence as listed in SEQ ID NO:1, which underwent partial mutation such as deletion, substitution, addition or modification, may be used.

The DNA fragment of the present invention may be isolated from a bacterium belonging to the genus Bacillus, preferably *Bacillus stearothermophilus* and more preferably *Bacillus stearothermophilus* ATCC 12016 strain by a conventional method, or may be chemically synthesized by a conventional method.

For example, the DNA fragment of the present invention is prepared as in the following. First, a chromosomal DNA of a bacterium belonging to the genus Bacillus, preferably *Bacillus stearothermophilus* ATCC 12016 is isolated and purified. Said DNA is cleaved by ultrasonication or with restriction enzyme and the DNA fragment obtained is ligated with a lineared expression vector at the blunt ends or cohesive ends of the both DNAs by the use of a DNA ligase etc. to give a recombinant vector. The recombinant vector thus obtained is introduced into a replicatable host to construct a gene library. From this gene library, a microorganism (donor microorganism) carrying a recombinant vector having a heat-resistant MAD-encoding DNA is obtained by screening with the use of a marker of the vector and heat-resistant MAD activity as indices. Then, the obtained donor microorganism is cultured under aeration for about 1 to 3 days in a liquid medium and the culture obtained is centrifuged to collect cells. The cells are lysed to give a lysate containing the heat-resistant MAD gene. For lysis, a lytic enzyme such as lysozyme or β-glueanase may be used along with, where necessary, protease, other enzyme or a surfactant such as sodium lauryl sulfate, or a physical treatment such as freeze-thawing or ultrasonication may be used together with the above-mentioned lyric treatment on demand.

DNA is isolated and purified by appropriately combining conventional methods such as deproteinization by extraction with phenol, protease treatment, treatment with ribonuclease and alcohol precipitation.

The obtained DNA is prepared into a DNA fragment of the present invention by ultrasonic treatment, treatment with restriction enzyme and the like, preferably by the treatment with a II-type restriction enzyme.

The recombinant vector of the present invention has the aforementioned DNA fragment of the present invention and is preferably capable of autonomic proliferation in *E. coli* or *Bacillus subtilis*.

The recombinant vector of the present invention is preferably an expression vector inducing the host cell (e.g. *E. coli, Bacillus subtilis*) to express the gene encoding the heat-resistant MAD for the production of the heat-resistant MAD.

Said recombinant vector is prepared by integrating the DNA fragment of the present invention into a vector for expression with ease.

Preferable vector for expression is that for use in genetic recombination, which is constructed from a phage or a plasmid capable of autonomic proliferation in a host microorganism.

Examples of the phage when, for example, *E. coli* is used as a host microorganism include λgt 10 and λgt 11.

Examples of the plasmid when, for example, *E. coli* is used as a host microorganism include pBR322 and pUC19. When *Bacillus subtilis* is used as a host microorganism, pUB110, pC19 or the like may be used. In addition, a shuttle vector (e.g. pHY300PLK) capable of autonomic proliferation in two or more Gram negative or Gram positive host microorganisms such as *E. coli* and *Bacillus subtills* may be used.

So as to give a lineared vector fragment, it is preferable that such vector for expression should be cleaved with the same restriction enzyme as that used for the cleavage of the donor microorganism mentioned earlier. The DNA fragment of the present invention is ligated with said vector fragment by a conventional method using DNA ligase. For example, a cohesive end or a blunt end of the DNA fragment of the present invention is annealed with that of the vector fragment and ligated with them by the use of a suitable DNA ligase to construct a recombinant vector having the DNA fragment of the present invention. Where necessary, the annealed DNA fragment-vector fragment is introduced into a host microorganism to allow biological DNA ligase to construct a recombinant vector therefrom.

The transformant of the present invention is transformed with the aforementioned recombinant vector of the present invention and can be prepared by introducing said recombinant vector into a host microorganism by a conventional method.

The host microorganism may be any insofar as the recombinant vector of the present invention can be present stably therein, is capable of autonomic proliferation therein and extraneous gene is capable of transformation therein, and examples thereof include *E. coli* W3110, *E. coli* C600, *E. coli* JM109, *Bacillus subtilis* MI113 and *Bacillus subtills* MT-2.

A recombinant vector may be transformed into a host microorganism by, for example, recombinant DNA incorporation in the presence of a calcium ion when the host microorganism belongs to the genus *E. coli*, and by a competent cell method [J. Mol. Biol., 56, 209 (1971)], a protoplast method [Mol. Gen. Genet. 168, 111 (1979)] or electropolation [Cell, vol. 48, 813–825 (1987)] when the host microorganism belongs to the genus Bacillus. The transformant microorganism thus obtained has been found to stably produce a large amount of the protein having heat-resistant malate dehydrogenase activity when it is cultured in a nutrient medium. The selection of the host microorganism with respect to the transformation of the object recombinant vector may be based on a search for a host microorganism capable of concurrently expressing both a drug resistant marker and the heat-resistant MAD of the vector carrying the object DNA. For example, a microorganism capable of growing in a medium containing the drug, the medium being selected according to the drug resistant marker, as well as producing heat-resistant MAD may be selected.

So as to distinguish over the heat-labile malate dehydrogenase derived from the host microorganism, the heat-resistant MAD of the present invention is detected as follows. That is, cultured cells are disrupted and treated with heat at 65° C. for 30 minutes to completely inactivate the malate dehydrogenase derived from the host microorganism, whereafter the malate dehydrogenase activity caused by the heat-resistant MAD of the present invention is determined.

The recombinant vector of the present invention carrying the heat-resistant MAD gene is taken out from the transformant microorganism and can easily transform other microorganism. It can also be easily done to cleave out the heat-resistant MAD gene from the recombinant vector of the present invention carrying the heat-resistant MAD gene by the use of a restriction enzyme etc., ligating same with a vector fragment obtained by cleaving in the same manner as above and transforming the host microorganism.

According to the method of the present invention, a heat-resistant MAD is produced by culturing the aforementioned transformant of the present invention. The culture is done under the conditions selected in view of the nutritive-biological properties of the host and liquid culture is generally selected, though from an industrial viewpoint, aerobic spinner culture is advantageous. The carbon source of the medium may be any that is widely used for culture of transformants, insofar as the host microorganism can utilize same, such as glucose, sucrose, lactose, maltose, fructose, honey and pyruvic acid. The nitrogen source may be any that is utilizable by the host microorganism, such as organic nitrogen compound (e.g. pepton, meat extract, yeast extract, hydrolysate of casein, soybean lees extracted with alkali) and inorganic nitrogen compounds such as ammonium sulfate and ammonium chloride. Besides these, usable as necessary are salts such as phosphate, carbonate, sulfate, magnesium, calcium, potassium, iron, manganese and zinc, particular amino acids and particular vitamins.

The temperature of culture may be appropriately varied within the range wherein the host microorganism grows and produces the heat-resistant MAD. In the case of *E. coli*, it is preferably about 20°–42° C. While the culture period somewhat varies depending on culture conditions, the culture may be terminated when the yield of the heat-resistant MAD has reached maximum, which is about 20–48 hours. The pH of the medium may be varied within the range wherein the host microorganism grows and produces the heat-resistant MAD, which is preferably about pH 6.0–9.0.

The cells are recovered from a liquid culture by a conventional method such as centrifugation and filtration. When the heat-resistant MAD in the liquid culture is secreted outside the cells, the cell-removed culture can be used, from which the heat-resistant MAD is isolated and purified by the following method subsequent to cell lysis.

When the heat-resistant MAD is present intracellularly, it can be extracted upon lysis by enzymatic or physical treatment as mentioned above. The thus-obtained solution containing the heat-resistant MAD is treated with heat at a temperature permitting inactivation of the malate dehydrogenase derived from the host but not permitting inactivation of the target heat-resistant MAD (for example, the treatment at 65° C. for 30 minutes) to remove the malate dehydrogenase derived from the host. Then, the nucleic acid is removed by a treatment with a hydrophilic polymer such as polyethyleneimine and the heat-resistant MAD fraction is recovered by precipitation with ammonium sulfate.

The recovered heat-resistant MAD solution is subjected to a heat treatment for a long time under the conditions which do not cause inactivation of the target heat-resistant MAD, for example, a treatment at 60° C. for 16 hours to denature the contaminant protein derived from the host to allow removal thereof as an insoluble protein. The insoluble protein is removed by a conventional method such as centrifugation or filtration.

The heat-resistant MAD solution is subjected to desalting by a conventional method, such as dialysis using a semi-permeable membrane or gel filtration on Sephadex G-25 (Pharmacia LKB, Sweden).

The heat-resistant MAD solution is then adjusted to pH 4.0 with an acid solution such as acetic acid solution and separated and purified by column chromatography such as ion exchange chromatography, preferably CM-Sepharose CL-6B (Pharmacia LKB, Sweden) to give a purified heat-resistant MAD product. This product migrates as a single band on SDS-PAGE.

The heat-resistant MAD to be obtained by the method of the present invention has a residual activity after preservation at 40° C. for 10 days in a solution state of at least 60%, preferably 70% more preferably 80% and most preferably 90%, and preferably has the following properties.

Action: reversibly catalyzes the following reaction.

L-malic acid+$NAD^+$ ⇌ oxaloacetic acid+NADH+$H^+$

Substrate specificity: Specifically oxidizes L-malic acid or specifically reduces oxaloacetic acid.

Optimum temperature: 70° C.

Optimum pH: 8.0

Heat stability: not more than 70° C.

pH Stability: pH 3.0–9.0

Isoelectric point: 4.8

Molecular weight: 140,000 (gel filtration), 38,000 (SDS-PAGE)

Km value: $4.3 \times 10^{-6}$M (oxaloacetic acid)

Specific activity: 203 U/mg protein

This heat-resistant MAD differs from the heat-resistant MAD produced by *Bacillus stearothermophilus* ATCC 12016 in terms of heat stability and specific activity. That is, the heat-resistant MAD produced by *Bacillus stearothermo-*

*philus* ATCC 12016 exhibits heat stability of not more than 65° C. and specific activity of 103 U/mg protein, whereas the heat-resistant MAD produced by the transformant having the maleate dehydrogenase activity exhibits heat stability of not more than 70° C. and specific activity of 203 U/mg protein.

The reagent for GOT determination of the present invention is characterized by the aforementioned heat-resistant MAD of the present invention and is superior in long-term storability. Besides the heat-resistant MAD, the reagent contains NADH, α-ketoglutaric acid and L-aspartic acid, and optionally lactate dehydrogenase.

While the lactose dehydrogenase is not directly involved with the GOT reaction, it is useful for determining the oxaloacetic acid produced in the first reaction in the GOT determination. That is, the presence of lactose dehydrogenase prevents change of oxaloacetic acid to pyruvic acid by decarboxylation, which in turn aids precise determination of $NAD^+$ conversion velocity, i.e. GOT amount (Japanese Patent Unexamined Publication Nos. 39799/1982, 53298/1982, 175898/1984).

The lactate dehydrogenase to be used in the present invention may be of any origin insofar as the residual activity after preservation at 40° C. for 10 days in a solution state is at least 60%. For example, those derived from animal organs such as bovine heart or swine heart and those derived from lactic acid bacteria are usable, with preference given to those derived from lactic acid bacteria which are superior in stability.

The reagent for GOT determination of the present invention may be a one component or two component solution. Example of the two component reagent is a mixture of a first reagent containing a heat-resistant MAD of the present invention, lactate dehydrogenase, NADH and α-ketoglutaric acid or L-aspartic acid and a second reagent containing L-aspartic acid or α-ketoglutaric acid.

An exemplary composition of the reagent of the present invention is shown below. The figures express concentration or enzyme activity obtained after mixing the first reagent and the second reagent.

| | |
|---|---|
| Lactate dehydrogenase (optional) | 500–2000 U/l |
| Heat-resistant MAD of the invention | 500–5000 U/l |
| L-Aspartic acid | 150–250 mmol/l |
| α-Ketoglutaric acid | 10–40 mmol/l |
| NADH | 0.1–0.25 mmol/l |
| Buffer | 0.05–0.1 mmol/l |

As the buffer, desirable are Tris-HCl, sodium phosphate, potassium phosphate and GOOD buffer. The reagent of the present invention preferably has a pH of 7.0–8.0.

The method of the present invention for determining GOT activity is characterized by the use of the aforementioned reagent for GOT determination. The method comprises bringing a GOT determination test sample into contact with a reagent of the present invention and determining, based on the decrease in absorbance at 340 nm, the conversion speed of NADH in the reagent into $NAD^+$ through the reactions of L-aspartic acid + and

In general, GOT activity unit per 1 l of a sample is calculated as follows.

$$GOT\ activity(U/l) = \frac{(\Delta A/min) \times dilution\ of\ sample}{\mu mol\ molecular\ absorbance\ coefficient\ of\ NADH}$$

The GOT IU (international unit) is defined as an enzyme amount necessary for consuming 1 μmol of NADH per minute at 30° C.

The protein of the present invention is a novel, heat-resistant MAD having a residual activity after preservation at 40° C. for 10 days in a solution state of at least 60%. According to the present invention, the nucleotide sequence of the heat-resistant malate dehydrogenase has been clarified and industrial mass production thereof has become attainable.

The production method of the present invention, moreover, has enabled production of a heat-resistant MAD having higher purity than and superior heat stability to the heat-resistant MAD produced by a wild type strain ATCC 12016.

According to the present invention, a reagent for GOT determination which is superior in long-term storage, can be prepared by the use of the heat-resistant MAD having a residual activity upon preservation at 40° C. for 10 days in a solution state of at least 60%. The reagent of the present invention is extremely advantageous in view of the fact that liquid reagents are increasingly used in many fields, since it is stable in a liquid state.

The present invention is hereinafter explained in detail by way of Examples.

In the Examples, activity of the heat-resistant MAD was determined as in the following.

The heat-resistant MAD was reacted in 97 mM potassium phosphate buffer (pH 7.5), 0.49 mM oxaloacetic acid and 0.2 mM NADH at 25° C. for 3–4 minutes and absorbance at 340 nm was determined. One unit of the enzyme activity is an enzyme amount necessary for oxidizing 1 μmol NADH per minute under these conditions.

EXAMPLE 1

Purification of heat-resistant MAD from *Bacillus stearothermophilus* ATCC 12016

*Bacillus stearothermophilus* ATCC 12016 was cultured in a jar fermenter. The culture was performed in an LB medium (1% polypepton, 0.5% yeast extract and 0.5% NACl, pH 7.4) containing 1% sodium acetate at 50° C. for 26 hours with aeration. The yield was about 1.2 U/ml. The culture obtained (5.2 l) was centrifuged to separate about 30 g of cells. The cells were suspended in 50 mM potassium phosphate buffer, pH 7.5, and lysed by the treatment with lysozyme to give about 2 l of cell lysate. The heat-resistant malate dehydrogenase activity at this time was about 3.1 U/ml. The lysate was subjected to denucleation by the treatment with polyethyleneimine, after which heat-resistant MAD fraction was recovered by precipitation with ammonium sulfate and resuspended in 50 mM potassium phosphate buffer (pH 7.5). The specific activity at this time was 0.16 U/mg protein.

The suspension of ammonium sulfate precipitation was desalted with Sephadex G-25 (Pharmacia LKB, Sweden). The desalted solution was subjected to DEAE Sepharose CL-6B (Pharmacia LKB, Sweden) column chromatography bufferized with 50 mM potassium phosphate buffer, pH 7.5, and eluted with a gradient of between 0.15M and 0.35M NaCl. Then, the resultant solution was subjected to Phenyl Sepharose CL-6B (Pharmacia LKB) column chromatography bufferized with 50 mM potassium phosphate buffer (pH 7.5) containing ammonium sulfate having 0.15 saturation degree, washed with ammonium sulfate having 0.15–0.0 saturation degree and eluted with 0–50% ethylene glycol. Then, the enzyme solution was subjected to gel filtration through TSKgelG-3000SW (manufactured by Tokuyama Soda, Japan) bufferized with 50 mM potassium phosphate buffer (pH 7.5) containing 0.2M NaCl. Thereafter, the enzyme solution was subjected to MonoP HR5/5 chromatofocusing (Pharmacia LKB) and eluted with a gradient of between pH 6.0 and pH 4.5. The heat-resistant MAD product obtained by the present method showed a single band on SDS-PAGE and had specific activity of 108.0 U/mg protein.

The above-mentioned purifications are summarized in Table 1. The physicochemical properties of the heat-resistant MAD obtained by the method above are shown in Table 2.

TABLE 1

Purification of heat-resistant MAD from *Bacillus stearothermophilus* ATCC 12016

| step | total activity (U) | specific activity (U/mg-protein) | yield (%) |
| --- | --- | --- | --- |
| lysozyme-treated solution | 6200 | — | 100 |
| polyethyleneimine-treated solution | 5890 | 0.08 | 95 |
| resuspension of ammonium sulfate precipitation | 3250 | 0.16 | 52 |
| G-25-desalted solution | 3280 | 0.21 | 53 |
| DEAE Sepharose | 3470 | 0.76 | 56 |
| Phenyl Sepharose | 2770 | 12.0 | 45 |
| TSK G-3000SW | 2200 | 74.4 | 35 |
| MonoP HR5/5 | 1540 | 108.0 | 25 |

TABLE 2

Physicochemical properties of heat-resistant MAD purified from *Bacillus stearothermophilus* ATCC 12016

| item | |
| --- | --- |
| Action | L-Malate + NAD$^+$ ⇌ Oxaloacetate + NADH + H$^+$ |
| Substrate specificity | specific oxidation of L-malic acid or specific reduction of oxaloacetic acid |
| Optimum temperature | 65° C. |
| Optimum pH | pH 8.0 |
| Heat stability | not more than 65° C. |
| pH stability | pH 3.0–9.0 |
| Isoelectric point | 4.8 |
| Molecular weight | 140,000(gel filtration) 38,000(SDS-PAGE) |
| Km value | 5.0 × 10$^{-6}$ M (oxaloacetic acid) |
| Specific activity | 108 U/mg-protein |

EXAMPLE 2

Isolation of chromosomal DNA

The chromosomal DNA of *Bacillus stearothermophilus* ATCC 12016 was isolated by the following method.

The cell was subjected to shake culture in 150 ml of bouillon medium at 60° C. overnight and the culture was centrifuged (8000 rpm, 10 min) to collect cells. The cells were suspended in a solution (5 ml) containing 10% sucrose, 50 mM Tris-HCl (pH 8.0) and 50 mM EDTA and 1 ml of lysozyme solution (10 mg/ml) was added thereto. The mixture was incubated at 3° C. for 15 minutes and 1 ml of 10% SDS solution was added thereto. An equivalent amount of chloroform-phenol solution (1:1) was added thereto ad the mixture was stirred. The mixture was subjected to centrifugation at 10,000 rpm for 3 minutes to separate a water layer from a solvent layer and the water layer was partitioned. A 2-fold amount of ethanol was gently layered on the water layer and DNA was isolated by winding same around a glass rod which was gently whirled therein.

The DNA was dissolved in 10 mM Tris-HCl buffer, pH 8.0, containing 1 mM EDTA (hereinafter abbreviated as TE), which was then treated with an equivalent amount of chloroform-phenol solution. Centrifugation of the resultant solution separated a water layer and a two-fold amount of ethanol was added thereto. In the same manner as above, DNA was again isolated and dissolved in 2 ml of TE.

The competent cell of *Eschelichia coli* JM109 was prepared by the method of Hanahan [Proc. Natl. Acad. Sci., USA, 75, 1927 (1978)] and used as a host for the construction of a library.

EXAMPLE 3

Preparation of DNA fragment comprising a gene encoding heat-resistant MAD and recombinant vector comprising said DNA fragment DNA (1 μg) as obtained in Example 2 was partially disintegrated with restriction enzyme Sau3AI (manufactured by Toyo Boseki Kabushiki Kaisha, Japan) into fragements of not less than 2 kbp. The DNA fragment was ligated with pUC19 (0.5 μg) cleaved with SalI (manufactured by Toyo Boseki Kabushiki Kaisha, Japan) by a reaction with 1 unit of T4DNA ligase (manufactured by Toyo Boseki Kabushiki Kaisha, Japan) at 16° C. for 12 hours according to the backfilling method of M. G. Loftus et al. [Biotechniques Vol. 12, No. 2 (1992)]. The ligated DNA was transformed with competent cell of *Eschelichia coli* JM109. The colonies of the transformant were obtained at about 1×10$^6$ per 1 μg of the DNA used.

The obtained colonies were cultured in an LB medium (5 ml, 1% polypepton, 0.5% yeast extract, 0.5% sodium chloride) containing 50 μg/ml ampicillin at 37° C. for 18 hours and the culture was centrifuged (12,000 rpm, 3 min) to collect cells. The cells were screened to give a transformant having a heat-resistant malate dehydrogenase activity.

That is, the collected cells were suspended in 1 ml of 0.1M potassium phosphate (pH 7.5) and the cells in the suspension were disrupted with glass beads. After disrupting, the resultant suspension was subjected to centrifugation (12,000 rpm, 5 min) to remove cell residue. The obtained crude enzyme solution was heated at 65° C. for 30 minutes and malate dehydrogenase activity was determined.

Figure 1:
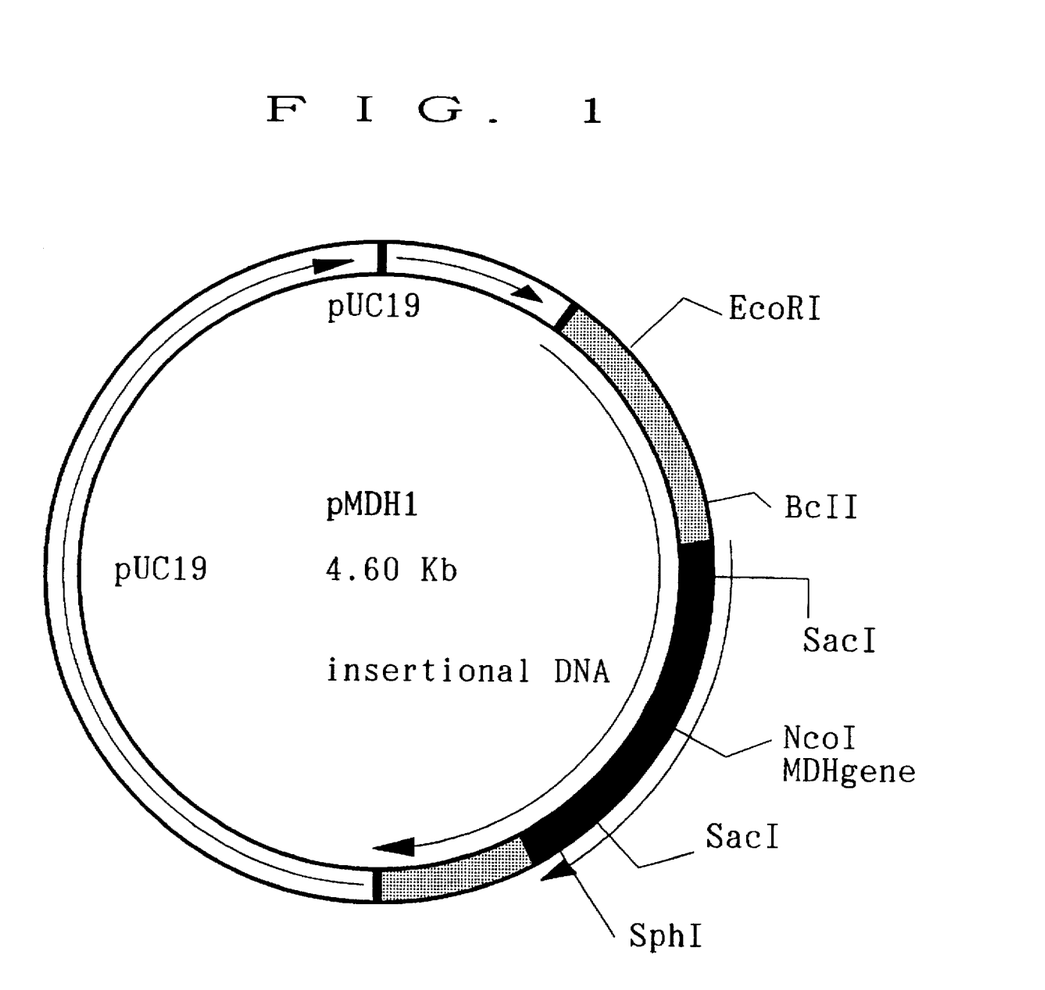
FIG. 1 is a restriction enzyme map of an insertional DNA of pMDH1.

As a result of screening of about 10,000 colonies, one strain capable of producing heat-resistant MAD was found. The plasmid of the strain was found to contain an about 1.9 kbp insertional DNA and the plasmid was named pMDH1. The restriction enzyme map of the insertional DNA of pMDH1 is shown in FIG. 1.

EXAMPLE 4

Determination of nucleotide sequence

A subclone was prepared by cleaving about 1.9 kbp insertional DNA of pMDH1 with various restriction enzymes. The nucleotide sequence of the various subclones was identified by a conventional method with the use of Chemiluminescent DNA Sequencing Kit (manufactured by Toyo Boseki Kabushiki Kaisha, Japan). The identified nucleotide sequence and amino acid sequence are shown in Sequence Lists. The molecular weight determined based on the amino acid sequence was about 35,500 which was very close to the molecular weight (about 38,000) of malate dehydrogenase from *Bacillus stearothermophilus* ATCC 12016.

EXAMPLE 5

Preparation of *Escherichia coli* transformant

The competent cell of *Eschelichia coli* JM109 was transformed with pMDH1 to give a transformant JM109 (pMDH1).

EXAMPLE 6

Production of heat-resistant MAD

The above-mentioned LB medium (6 l) was dispensed to a 10 l-jar fermenter and autoclaved at 121° C. for 15 minutes. After cooling, 6 ml each of 50 mg/ml ampicillin (manufactured by Nakarai Tesque, Japan) and 200 mM IPTG (manufactured by Nihon Seika Corp., Japan), separately sterilized by filtration, was added thereto. A culture (60 ml) of *Escherichia coil* JM109 (pMDH1) cultured in a medium having the same composition as above at 37° C. for 18 hours was inoculated to the above medium and the medium was cultured with aeration at 37° C. for 19 hours. The heat-resistant malate dehydrogenase activity after culture was 7.7 U/ml.

The culture (6 l) was subjected to centrifugation to collect cells and the cells were suspended in 280 ml of 50 mM potassium phosphate buffer (pH 7.5) and disrupted in a Dynomill (manufactured by WAB, Switzerland) by a conventional method. The resultant suspension was centrifuged at 8,000 rpm for 20 minutes to give a crude enzyme solution of heat-resistant MAD. The crude enzyme solution thus obtained was treated at 65° C. for 30 minutes to inactivate the malate dehydrogenase derived from the host and denucleated with polyethyleneimine. The heat-resistant MAD fraction was recovered by precipitation with ammonium sulfate and resuspended in the above-mentioned buffer (16 ml). The resuspension was heated at 60° C. for 16 hours. After the heat treatment, the resultant suspension was desalted with Sephadex G-25. The desalted enzyme solution was adjusted to pH 4.0 with acetic acid and subjected to CM Sepharose CL-6B (Pharmacia LKB, Sweden ) chromatography to give a purified heat-resistant MAD product. The heat-resistant MAD product which underwent CM Sepharose CL-6B chromatography migrated as a single band on SDS-PAGE and the activity yield was 49%.

The purification from the transformant is summarized in Table 3. The physicochemical properties of the heat-resistant MAD obtained by the above method are shown in Table 4.

TABLE 3

Purification of heat-resistant MAD from *Escherichia coli* JM109 (pMDH1)

| step | total activity (U) | specific activity (U/mg-protein) | yield (%) |
|---|---|---|---|
| Dynomill disrupted solution | 46200 | — | 100 |
| heat-treated solution I | 37800 | 4.56 | 82 |
| polyethyleneimine-treated solution | 37400 | 6.46 | 81 |
| resuspension of ammonium sulfate precipitation | 37700 | 34.1 | 82 |
| heat-treated solution II | 32400 | 40.9 | 70 |
| G-25 desalted solution | 31800 | 83.0 | 69 |
| acid-treated solution | 31800 | 105.3 | 69 |
| CM Sepharose | 22800 | 203.0 | 49 |

TABLE 4

Physical and chemical properties of heat-resistant MAD from *Escherichia coli* JM109 (pMDH1)

| item | |
|---|---|
| Action | L-Malate + NAD$^+$ ⇌ Oxaloacetate + NADH + H$^+$ |
| Substrate specificity | specific oxidation of L-malic acid or specific reduction of oxaloacetic acid |
| Optimum temperature | 70° C. |
| Optimum pH | pH 8.0 |
| Heat stability | not more than 70° C. |
| pH stability | pH 3.0–9.0 |
| Isoelectric point | 4.8 |
| Molecular weight | 140,000(gel filtration) 38,000(SDS-PAGE) 35,500 (amino acid sequence) |
| Km value | 4.3 × 10$^{-6}$ M (oxaloacetic acid) |
| Specific activity | 203 U/mg-protein |

A comparison of Table 1 and Table 3 readily indicates that the method for producing the heat-resistant MAD of the present invention enables production of the enzyme at higher purity in a larger amount as compared with the enzyme purified from wild type *Bacillus stearothermophilus* ATCC 12016.

In addition, a comparison of Table 2 and Table 4 reveals that the heat-resistant MAD produced by the transformant is superior to the heat-resistant MAD produced by *Bacillus stearothermophilus* ATCC 12016 in terms of heat stability.

EXAMPLE 7

Preparation of reagent for GOT determination, comprising use of heat-resistant MAD derived from *Eschelichia coli* JM109 (pMDH1)

The following solution was prepared as a reagent for GOT determination.

| Lactate dehydrogenase | 500 U/l |
|---|---|
| Heat-resistant MAD | 1000 U/l |
| L-Aspartic acid | 200 mmol/l |
| α-Ketoglutaric acid | 10 mmol/l |
| NADH | 0.16 mmol/l |
| Tris-HCl buffer (pH 7.5) | 80 mmol/l |

The heat-resistant MAD was prepared from *Eschelichia coli* JM109 (pMDH1) by the method of Example 6.

Figure 2:
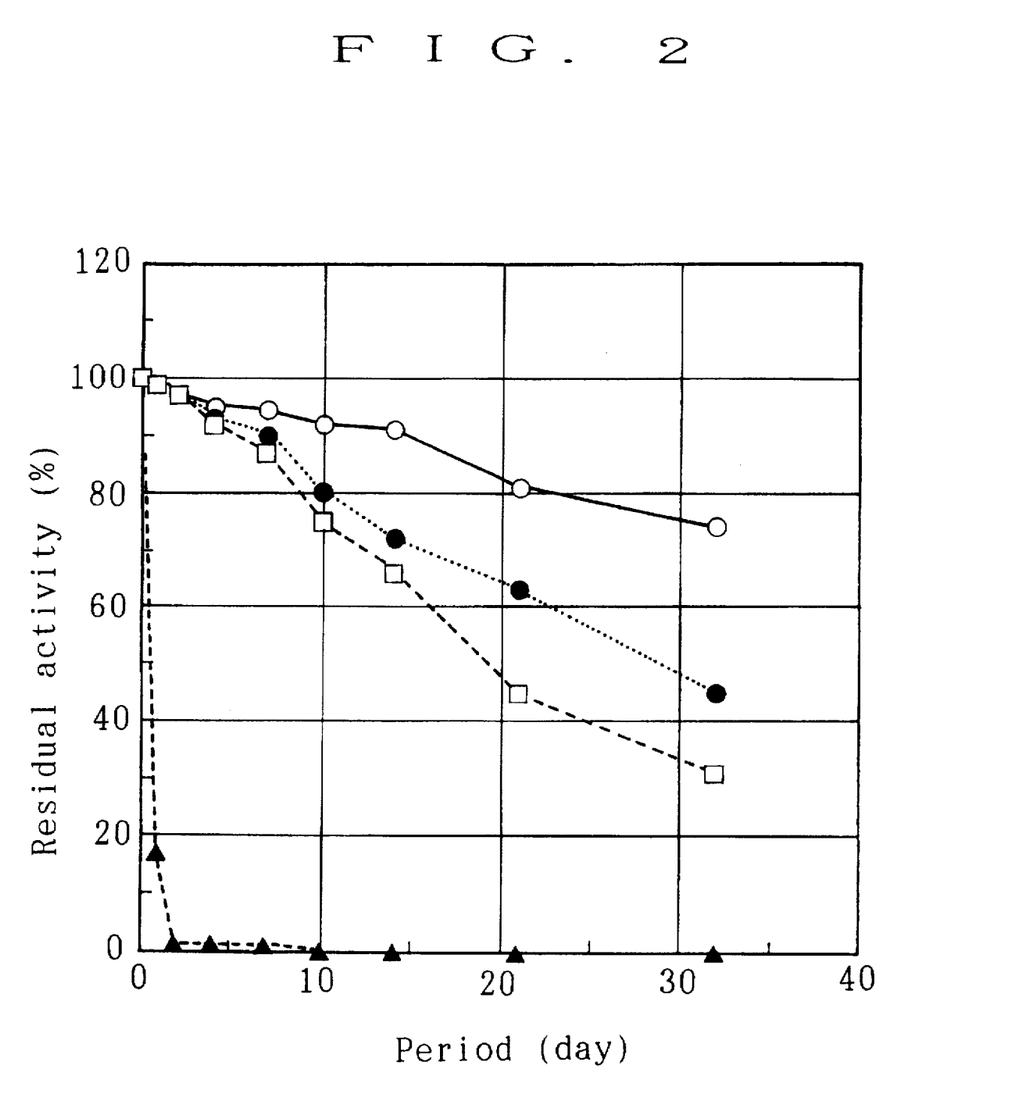
FIG. 2 shows residual malate dehydrogenase activity as determined in Examples 7 and 8, and Comparative Examples 1 and 2.

The above-mentioned reagent was stored at 40° C. and residual malate dehydrogenase activity was measured at 1, 2, 4, 7, 10, 14, 21 and 32 days of storage. The results are shown in FIG. 2 with ○ and the activity was retained by 99% by 1-day storage, 97% by 2-day storage, 95% by 4-day storage, 94% by 7-day storage, 92% by 10-day storage, 91% by 14-day storage, 81% by 21-day storage and 74% by 32-day storage.

Figure 3:
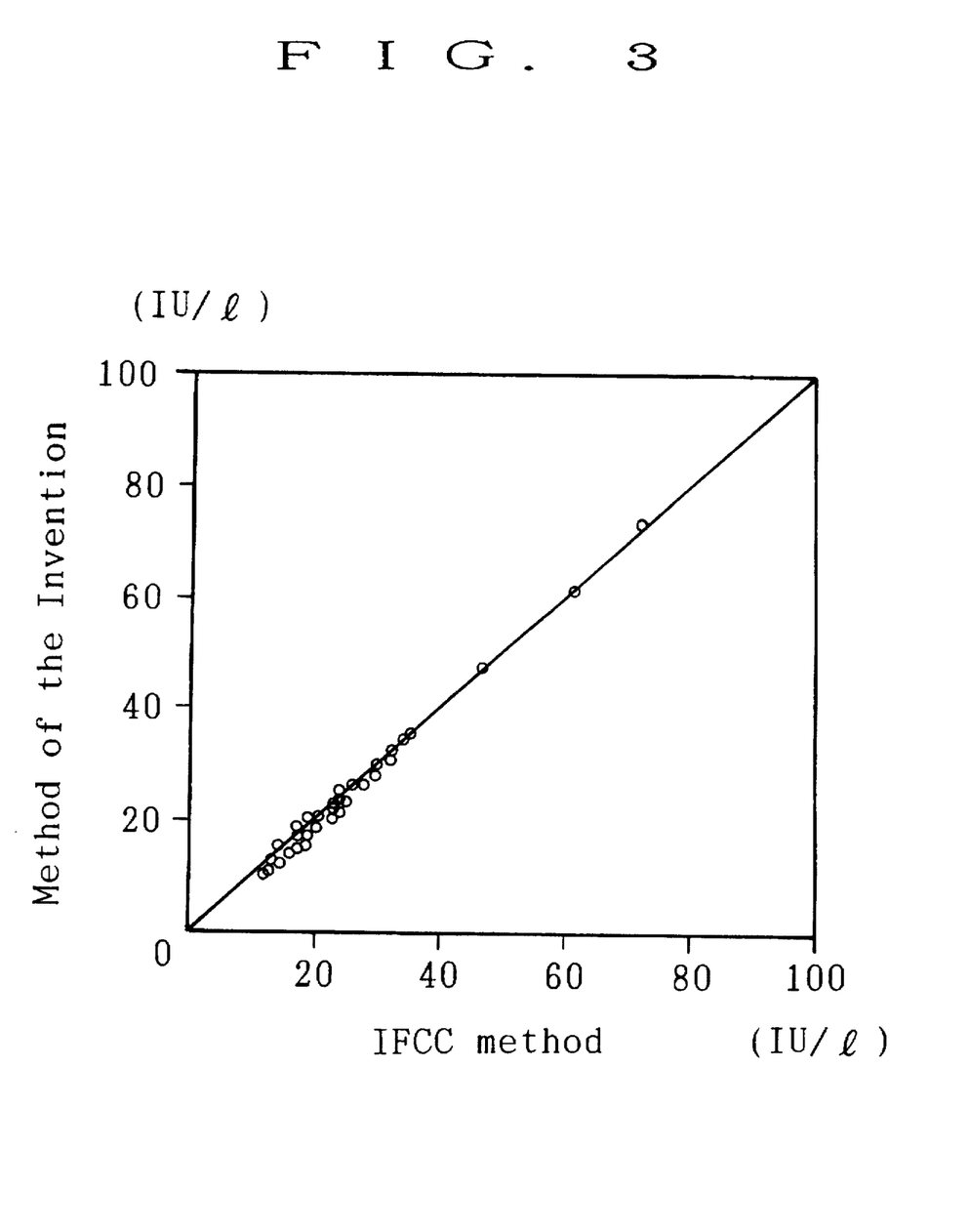
FIG. 3 shows a correlation between the determination of GOT activity in serum using the reagent of the present invention and the determination by IFCC method using the MAD of the present invention.

The correlation between the determination of GOT in serum using the above-mentioned reagent and the determination by IFCC (International Federation of Clinical Chemistry) method is shown in FIG. 3, which was found to be superior.

EXAMPLE 8

Preparation of reagent for GOT determination, using heat-resistant MAD derived from *Bacillus stearothermophilus* ATCC 12016.

As the reagent for GOT determination, a solution of the composition of Example 7 was prepared. Note that an enzyme prepared by the method of Example 1 from *Bacillus stearothermophilus* ATCC 12016 was used as the heat-resistant MAD.

The above-mentioned reagent was stored at 40° C. and residual malate dehydrogenase activity was measured at 1, 2, 4, 7, 10, 14, 21 and 32 days of storage. The results are shown in FIG. 2 with ● and the activity was retained by 99% by 1-day storage, 97% by 2-day storage, 93% by 4-day storage, 90% by 7-day storage, 80% by 10-day storage, 72% by 14-day storage, 63% by 21-day storage and 45% by 32-day storage.

Comparative Example 1

Preparation of reagent for determining GOT activity, using malate dehydrogenase derived from swine heart As the reagent for GOT determination, a solution of the composition of Example 7 was prepared. Note that a commercially available enzyme derived from swine heart was used in place of the heat-resistant MAD.

The above-mentioned reagent was stored at 40° C. and residual malate dehydrogenase activity was measured at 1, 2, 4, 7, 10, 14, 21 and 32 days of storage. The results are shown in FIG. 2 with ▲ and the activity was retained by 17% by 1-day storage, 2% by 2-day storage, 1% by 4-day storage, 1% by 7-day storage, 0% by 10-day storage, 0% by 14-day storage, 0% by 21-day storage and 0% by 32-day storage.

Comparative Example 2

Preparation of reagent for GOT determination, using malate dehydrogenase derived from the strain of the genus Thermus As the reagent for GOT determination, a solution of the composition of Example 7 was prepared. Note that a commercially available enzyme derived from the strain of the genus Thermus was used in place of the heat-resistant MAD.

The above-mentioned reagent was stored at 40° C. and residual malate dehydrogenase activity was measured at 1, 2, 4, 7, 10, 14, 21 and 32 days of storage. The results are shown in FIG. 2 with □ and the activity was retained by 99% by 1-day storage, 97% by 2-day storage, 92% by 4-day storage, 87% by 7-day storage, 75% by 10-day storage, 66% by 14-day storage, 45% by 21-day storage and 31% by 32-day storage.

The results indicate the superior stability of the heat-resistant MAD produced by the transformant, into which a gene derived from a bacterium belonging to the genus Bacillus has been incorporated, while being contained in the reagent for GOT determination.

What is claimed is:

1. An isolated DNA fragment having a nucleotide sequence encoding the amino acid sequence depicted in SEQ ID NO:2.

2. An isolated DNA fragment having a nucleotide sequence depicted in SEQ ID NO:1.

3. A recombinant vector having the DNA fragment of any one of claims 1 or 2.

4. The recombinant vector of claim 3, which is capable of autonomic proliferation in *Escherichia coli* or *Bacillus subtilis*.

5. A microorganism transformed with the recombinant vector of claim 3.

6. A strain of *Escherichia coli* or *Bacillus subtills* transformed with the recombinant vector of claim 4.

7. A method for producing a protein having a heat-resistant malate dehydrogenase activity, which shows a residual activity of at least 60% after preserving at 40° C. for 10 days in a solution state and which further has the following properties:

Action: reversibly catalyzing the following reaction;
L-maleic acid+$NAD^+$—oxaloacetic acid+NADH+$H^+$ Substrate specificity: specific oxidation of L-maleic acid or specific reduction of oxaloacetic acid pH stability: pH 3.0–9.0

Molecular weight: 140,000 (gel filtration), 38,000 (SDS-PAGE). comprising culturing the microorganism of claim 5 in a medium to produce said protein and harvesting said protein.

8. A method for producing a protein having a heat-resistant malate dehydrogenase activity, which shows a residual activity of at least 60% after preserving the protein at 40° C. for 10 days in a solution state, said method comprising culturing the microorganism of claim 5 in a medium to produce a protein having a heat-resistant malate dehydrogenase activity, and harvesting said protein.

9. A method according to claim 8, wherein said protein has a residual activity of at least 70% after preserving the protein at 40° C. in a solution state.

10. A method according to claim 8, wherein said protein has a residual activity of at least 80% after preserving the protein at 40° C. in a solution state.

11. A method according to claim 8, wherein said protein has a residual activity of at least 90% after preserving the protein at 40° C. in a solution state.

12. A method for producing a protein having a heat-resistant malate dehydrogenase activity, which shows a residual activity of at least 60% after preserving the protein at 40° C. for 10 days in a solution state, said method comprising culturing the strain of claim 6 in a medium to produce a protein having a heat-resistant malate dehydrogenase activity, and harvesting said protein.

13. A method according to claim 12, wherein said protein has a residual activity of at least after preserving the protein at 40° C. in a solution state.

14. A method according to claim 12, wherein said protein has a residual activity of at least after preserving the protein at 40° C. in a solution state.

15. A method according to claim 12, wherein said protein has a residual activity of at least after preserving the protein at 40° C. in a solution state.

* * * * *

UNITED STATES PATENT AND TRADEMARK OFFICE
CERTIFICATE OF CORRECTION

PATENT NO. : 5,686,294
DATED : November 11, 1997
INVENTOR(S) : Sogabe et al.

It is certified that error appears in the above-identified patent and that said Letters Patent is hereby corrected as shown below:

ON THE TITLE PAGE:

[56] References Cited: In Column 1, line 8: "Propertieis" should read --Properties--.
In Column 2, line 16: "Sloning" should read --Cloning--.
In Column 2, line 17: "11-3" should read --11.3--.

In Column 1, line 44: "subtills" should read --subtilis--.
In Column 1, line 54: "thermophilie" should read --thermophilic--.
In Column 1, line 63: "Thermus sp." Should read --*Thermus sp.*--.
In Column 4, lines, 19, 30 and 37: "Bacillus" should read --*Bacillus*--.
In Column 5, lines 50 and 57: "Bacillus" should read --*Bacillus*--.
In Column 6, line 7: "glueanase" should read --glucanase--.
In Column 6, line 45: "subtills" should read --subtilis--.
In Column 7, line 4: "subtills" should read --subtilis--.
In Column 7, line 13: "Bacillus" should read --*Bacillus*--.
In Column 9, line 66: "1" should read --*ℓ*--.
In Column 10, lines 47 and 50: "1" should read --*ℓ*--.
In Column 11, line 63: "3°" should read --37°--.
In Column 11, line 65: "ad" should read --and--.
In Column 13, lines 12, 13, and 24: "1" should read --*ℓ*--.
In Column 16, lines 7 and 11: "Thermus" should read --*Thermus*--.
In Column 16, line 24: "Bacillus" should read --*Bacillus*--.

UNITED STATES PATENT AND TRADEMARK OFFICE
CERTIFICATE OF CORRECTION

PATENT NO. : 5,686,294
DATED : November 11, 1997
INVENTOR(S) : Sogabe et al.

It is certified that error appears in the above-identified patent and that said Letters Patent is hereby corrected as shown below:

IN THE CLAIMS:

In Claim 6, Column 21, line 26: "subtills" should read --subtilis--.
In Claim 13, Column 22, line 35: "least after" should read --least 70% after--.
In Claim 14, Column 22, line 38: "least after" should read --least 80% after--.
In Claim 15, Column 22, line 41: "least after" should read --least 80% after--.

Signed and Sealed this

Ninth Day of June, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,686,294
DATED : November 11, 1997
INVENTOR(S) : Sogabe et al

It is certified that error appears in the above-identified patent and that said Letters Patent is hereby corrected as shown below:

In Claim 15, Column 22, line 41: "least after" should read --least 90% after--.

Signed and Sealed this

Sixth Day of July, 1999

Q. TODD DICKINSON

*Attest:*

*Attesting Officer*     *Acting Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1912 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Bacillus stearothermophilus
        ( B ) STRAIN: ATCC12016

( x i ) SEQUENCE DESCRIPTION: SEQ ID NO:1:

```
AATCAACTAC  GCGATTGAAC  ACGGCCGCAA  GTCGGTGACG  CTCGTTCATA  AAGGAAACAT   60

TATGAAATTC  ACCGAAGGCG  CGTTTAAAAA  CTGGGGTTAT  GAATTGGCGG  AGGAAGAATT  120

CGCCGACAAA  GTGTTCACGT  GGGCGCAATA  CGACCGAATC  GTTGAAACGG  AAGGCAAGGA  180

AGCGGCGAAC  AAAGCGCTTG  CTGATGCGGA  ACGGTCCGGC  AAAATCATTA  TCAAAGATGT  240

CATCGCCGAC  ATCTTCCTGC  AACAAATTTT  GACGCGTCGC  GCGAATTTGA  CGTCATCGCG  300

ACGATGAACT  TAAACGCCGA  CTACATTTCC  GACGCGCTGG  CCGCTCAAGT  CGGCGGCATC  360

GGCATCGCGG  CGGGGGCCAA  CATCAACTAC  GAAACCGGCC  ACGCGATTTT  CGAAGCGACG  420

CACGGCACGG  CTGCCGAATA  CGCAGGCTTG  ACAAAGTCAC  CGTCGTCCGT  CATTCTCTCG  480

GCGTCATGAT  GTTTGAGCAT  CTTGGTTGGA  ACGAAGCAGC  GAAATTGATC  ATCAAAGCGA  540

TGGAGAAAAC  CATCGCCGCG  AAAATCGTCA  CGTATGACTT  CGCCCGCCTG  ATGGAAGGGG  600
```

```
CGACGGAAGT GAAATGCTCC GAATTTGCTG ATGCGCTCAT CCGCAATATG GACTAACCTT      660

TGAAGGAAAG GGATGGCAAA CG ATG GCG ATG AAA CGG AAA AAA ATC TCG GTG       712
                         Met Ala Met Lys Arg Lys Lys Ile Ser Val
                          1               5                      10

ATC GGC GCC GGA TTC ACG GGG GCG ACG ACG GCG TTC CTT TTG GCG CAA        760
Ile Gly Ala Gly Phe Thr Gly Ala Thr Thr Ala Phe Leu Leu Ala Gln
                15                  20                  25

AAA GAG CTC GGC GAC GTC GTG TTG GTC GAT ATT CCG CAG CTT GAG AAC        808
Lys Glu Leu Gly Asp Val Val Leu Val Asp Ile Pro Gln Leu Glu Asn
                30                  35                  40

CCA ACG AAA GGG AAG GCG CTC GAT ATG CTC GAG GCA AGC CCG GTG CTC        856
Pro Thr Lys Gly Lys Ala Leu Asp Met Leu Glu Ala Ser Pro Val Leu
        45                  50                  55

GGC TTT GAC GCG AAT ATC ATC GGC ACA TCG GAT TAC GCT GAC ACA GCC        904
Gly Phe Asp Ala Asn Ile Ile Gly Thr Ser Asp Tyr Ala Asp Thr Ala
        60                  65                  70

GAT TCC GAC ATC GTC GTC ATC ACA GCA GGC ATC GCC CGC AAG CCG GGC        952
Asp Ser Asp Ile Val Val Ile Thr Ala Gly Ile Ala Arg Lys Pro Gly
75                  80                  85                  90

ATG AGC CGC GAC GAT TTG GTG ACG ACG AAC CAA AAA ATT ATG AAG CAA       1000
Met Ser Arg Asp Asp Leu Val Thr Thr Asn Gln Lys Ile Met Lys Gln
                95                 100                 105

GTG ACG AAG GAA GTC GTC AAA TAC TCG CCG AAC TGC TAC ATC ATC GTC       1048
Val Thr Lys Glu Val Val Lys Tyr Ser Pro Asn Cys Tyr Ile Ile Val
            110                 115                 120

TTG ACG AAC CCG GTC GAT GCG ATG ACG TAT ACG GTC TTT AAG GAA TCC       1096
Leu Thr Asn Pro Val Asp Ala Met Thr Tyr Thr Val Phe Lys Glu Ser
            125                 130                 135

GGA TTC CCG AAA AAC CGC GTC ATC GGC CAG TCG GGC GTC TTG GAT ACG       1144
Gly Phe Pro Lys Asn Arg Val Ile Gly Gln Ser Gly Val Leu Asp Thr
        140                 145                 150

GCG CGC TTC CGC ACG TTC GTC GCC GAG GAG CTG AAC ATT TCG GTA AAA       1192
Ala Arg Phe Arg Thr Phe Val Ala Glu Glu Leu Asn Ile Ser Val Lys
155                 160                 165                 170

GAT GTC ACT GGG TTT GTT TTA GGC GGC CAT GGC GAT GAC ATG GTG CCG       1240
Asp Val Thr Gly Phe Val Leu Gly Gly His Gly Asp Asp Met Val Pro
                175                 180                 185

CTC GTC CGC TAC TCG TAC GCC GGC GGC ATT CCG CTC GAA AAA CTC ATT       1288
Leu Val Arg Tyr Ser Tyr Ala Gly Gly Ile Pro Leu Glu Lys Leu Ile
                190                 195                 200

CCG AAA GAT CGT TTG GAC GCC ATC GTT GAG CGG ACG CGC AAA GGC GGC       1336
Pro Lys Asp Arg Leu Asp Ala Ile Val Glu Arg Thr Arg Lys Gly Gly
        205                 210                 215

GGT GAA ATC GTC AAC CTG CTC GGC AAC GGC AGC GCC TAC TAC GCA CCG       1384
Gly Glu Ile Val Asn Leu Leu Gly Asn Gly Ser Ala Tyr Tyr Ala Pro
        220                 225                 230

GCC GCC TCG CTT GTC GAA ATG GTC GAA GCG ATT TTG AAA GAC CAG CGC       1432
Ala Ala Ser Leu Val Glu Met Val Glu Ala Ile Leu Lys Asp Gln Arg
235                 240                 245                 250

CGC ATT TTG CCG GCG ATC GCC TAC CTT GAA GGC GAA TAC GGC TAT GAA       1480
Arg Ile Leu Pro Ala Ile Ala Tyr Leu Glu Gly Glu Tyr Gly Tyr Glu
                255                 260                 265

GGC ATT TAT TTG GGC GTG CCG ACG ATC CTC GGC GGC AAC GGC ATC GAG       1528
Gly Ile Tyr Leu Gly Val Pro Thr Ile Leu Gly Gly Asn Gly Ile Glu
                270                 275                 280

AAA GTG ATC GAG CTC GAG CTG ACC GAA GAG GAA AAA GCG CGC TCG CCA       1576
Lys Val Ile Glu Leu Glu Leu Thr Glu Glu Glu Lys Ala Arg Ser Pro
        285                 290                 295

AAT CCG TCG AAT CCG TTA AAA ATG TCA TGC GCA TCG TGG AAT AGC GGC       1624
Asn Pro Ser Asn Pro Leu Lys Met Ser Cys Ala Cys Trp Asn Ser Gly
```

-continued

```
          300                    305                         310
GAG  GCA  AAA  ATT  CCG  GCA  TTG  CCC  GGA  TTT  TTG  TCC  CAC  AGT  CAA         1669
Glu  Ala  Lys  Ile  Arg  Ala  Leu  Pro  Gly  Phe  Leu  Ser  His  Ser  Gln
315                      320                      325

TGAAAGCGCT  TTCTAGACAA  CGAAGGGGTG  GGAACATGTT  GAAAAAACGA  AAGCTCGGGA          1729

GACCGATCGG  GGAAATTCAA  GCGGGGGAAA  AGCTCGTGTT  CCAAGCCGCC  ATCGAAGACA          1789

AAGACTTGCT  TCTTTATCTT  GGGCTGACGG  ATGATGCCAA  TCCGCTCTAT  ATCCAGCATG          1849

ATTATGCTTC  ACAGACGCCG  TTTGGAAAAC  CGGTCGTGCC  GCCGGTCATG  TTGACGGGGA          1909

TGA                                                                                1912
```

( 2 ) INFORMATION FOR SEQ ID NO:2:

( i ) SEQUENCE CHARACTERISTICS:
        ( A ) LENGTH: 329 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met  Ala  Met  Lys  Arg  Lys  Lys  Ile  Ser  Val  Ile  Gly  Ala  Gly  Phe  Thr
 1              5                        10                       15

Gly  Ala  Thr  Thr  Ala  Phe  Leu  Leu  Ala  Gln  Lys  Glu  Leu  Gly  Asp  Val
              20                       25                       30

Val  Leu  Val  Asp  Ile  Pro  Gln  Leu  Glu  Asn  Pro  Thr  Lys  Gly  Lys  Ala
         35                       40                       45

Leu  Asp  Met  Leu  Glu  Ala  Ser  Pro  Val  Leu  Gly  Phe  Asp  Ala  Asn  Ile
         50                       55                       60

Ile  Gly  Thr  Ser  Asp  Tyr  Ala  Asp  Thr  Ala  Asp  Ser  Asp  Ile  Val  Val
 65                       70                       75                       80

Ile  Thr  Ala  Gly  Ile  Ala  Arg  Lys  Pro  Gly  Met  Ser  Arg  Asp  Asp  Leu
                   85                       90                       95

Val  Thr  Thr  Asn  Gln  Lys  Ile  Met  Lys  Gln  Val  Thr  Lys  Glu  Val  Val
              100                      105                      110

Lys  Tyr  Ser  Pro  Asn  Cys  Tyr  Ile  Ile  Val  Leu  Thr  Asn  Pro  Val  Asp
         115                      120                      125

Ala  Met  Thr  Tyr  Thr  Val  Phe  Lys  Glu  Ser  Gly  Phe  Pro  Lys  Asn  Arg
         130                      135                      140

Val  Ile  Gly  Gln  Ser  Gly  Val  Leu  Asp  Thr  Ala  Arg  Phe  Arg  Thr  Phe
145                      150                      155                      160

Val  Ala  Glu  Glu  Leu  Asn  Ile  Ser  Val  Lys  Asp  Val  Thr  Gly  Phe  Val
              165                      170                      175

Leu  Gly  Gly  His  Gly  Asp  Asp  Met  Val  Pro  Leu  Val  Arg  Tyr  Ser  Tyr
         180                      185                      190

Ala  Gly  Gly  Ile  Pro  Leu  Glu  Lys  Leu  Ile  Pro  Lys  Asp  Arg  Leu  Asp
         195                      200                      205

Ala  Ile  Val  Glu  Arg  Thr  Arg  Lys  Gly  Gly  Gly  Glu  Ile  Val  Asn  Leu
         210                      215                      220

Leu  Gly  Asn  Gly  Ser  Ala  Tyr  Tyr  Ala  Pro  Ala  Ala  Ser  Leu  Val  Glu
225                      230                      235                      240

Met  Val  Glu  Ala  Ile  Leu  Lys  Asp  Gln  Arg  Arg  Ile  Leu  Pro  Ala  Ile
                   245                      250                      255

Ala  Tyr  Leu  Glu  Gly  Glu  Tyr  Gly  Tyr  Glu  Gly  Ile  Tyr  Leu  Gly  Val
              260                      265                      270

Pro  Thr  Ile  Leu  Gly  Gly  Asn  Gly  Ile  Glu  Lys  Val  Ile  Glu  Leu  Glu
```

```
                275                         280                            285

Leu  Thr  Glu  Glu  Glu  Lys  Ala  Arg  Ser  Pro  Asn  Pro  Ser  Asn  Pro  Leu
          290                      295                300

Lys  Met  Ser  Cys  Ala  Cys  Trp  Asn  Ser  Gly  Glu  Ala  Lys  Ile  Arg  Ala
305                      310                     315                      320

Leu  Pro  Gly  Phe  Leu  Ser  His  Ser  Gln
                    325
```